United States Patent [19]

Malen et al.

[11] 4,267,345
[45] May 12, 1981

[54] ARYLTRIFLUOROETHYLAMINES

[75] Inventors: Charles E. Malen, Fresnes; Pierre Roger, St-Cloud; Michel Laubie, Vaucresson, all of France

[73] Assignee: Science Union et Cie, Suresnes, France

[21] Appl. No.: 31,386

[22] Filed: Apr. 19, 1979

Related U.S. Application Data

[63] Continuation-in-part of Ser. No. 798,830, May 20, 1977, abandoned.

[30] Foreign Application Priority Data

May 24, 1976 [FR] France ............................ 76 15601

[51] Int. Cl.³ .................... A61K 31/42; C07D 263/08
[52] U.S. Cl. ..................................... 548/233; 544/53; 544/96; 544/297; 548/190; 548/301; 424/246; 424/250; 424/270; 424/272; 424/273 R; 424/248.56

[58] Field of Search ............... 260/307 F; 544/88, 96; 424/272, 248.56; 548/233

[56] References Cited

U.S. PATENT DOCUMENTS

| Re. 27,133 | 6/1971 | Middleton | 260/307 |
|---|---|---|---|
| 3,453,284 | 7/1969 | Harvey | 260/307 |
| 3,626,067 | 12/1971 | Harvey | 424/272 |

Primary Examiner—Anton H. Sutto
Attorney, Agent, or Firm—Gordon W. Hueschen

[57] ABSTRACT

Certain arylmethyl amines have been prepared wherein the "methyl" carbon is substituted with a polyfluoroalkyl radical. The compounds form acid addition salts, exist in resolvable stereoisomeric forms, and are useful for treating hypertension. Formulations for human and veterinary medicine are described, as well as methods of use.

6 Claims, No Drawings

ARYLTRIFLUOROETHYLAMINES

This application is a application of our previous patent application Ser. No. 798,830 filed on May 20, 1977, now abandoned.

PRIOR ART

The prior art may be illustrated by the U.S. patent application Ser. No. 585,024 to Malen and al.

SUMMARY

This invention relates to α-aryl (trifluoroethyl) amines of the formula I

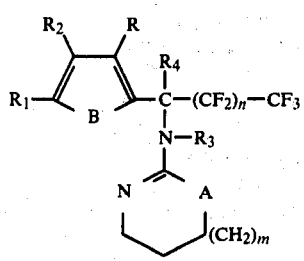

in which
A is oxygen, sulphur or an amino radical
B is CH=CH, oxygen, sulphur or an amino radical and
$R_1$, $R_2$, $R_3$ and R are either hydrogen or mineral or organic substituents.

The compounds of the formula I may be converted into an acid addition salt, preferably a therapeutically-compatible acid addition salt.

The compounds of the formula I may be in a racemic form or resolved into their optical isomers.

This invention also relates to the process for preparing the compounds fo formula I starting from a α-trifluoromethyl arylmethylamine of the formula II

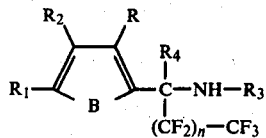

in which the meanings of the substituents remain the same as previously given.

This invention further relates to pharmaceutical compositions intended for human and veterinary medicine which comprises a compound of formula I or a salt thereof in admixture with an inert carrier or diluent.

The pharmaceutical compositions found an use for treating hypertension in mammals.

PREFERRED EMBODIMENTS

This invention relates to novel substituted aryl lower alkylamines. More precisely it relates to aryl methylamines, the methyl group of which is substituted by one or more polyfluoromethyl radicals.

This invention specifically provides the aryl (trifluoroethyl) amines of the formula I

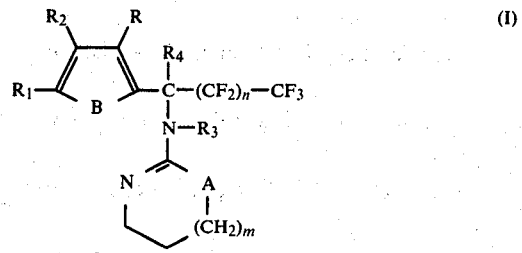

wherein
$R_1$ and $R_2$, the same or different, are hydrogen, a lower alkoxy radical, a lower alkylradical or a halogen.
$R_3$ is hydrogen, a methyl or an ethyl radical
$R_4$ is hydrogen, a methyl, an ethyl or a cyclopropyl radical
R is a hydrogen when $R_1$ and/or $R_2$ are different from hydrogen or is a lower alkyl when $R_1$ and/or $R_2$ are hydrogen
A is a heteroatom selected from the group consisting of oxygen, sulphur or an imino radical
B is bridge atom selected from the group consisting of —CH=CH—, oxygen, sulphur and the grouping >N—$R_5$ wherein $R_5$ is hydrogen or a lower alkyl radical
m is zero or 1
n is zero, 1 or 2

This invention also provides the salts of a compound of formula I with a mineral or organic acid, preferably a therapeutically-compatible mineral or organic acid.

This invention further provides the optically-active isomers of a compound of formula I or an acid addition salt thereof and preferably the levorotatory isomers.

Among the compounds of formula I it may be particularly cited:

(a) The oxazolines of formula $I_A$, in a racemic or optically-active form

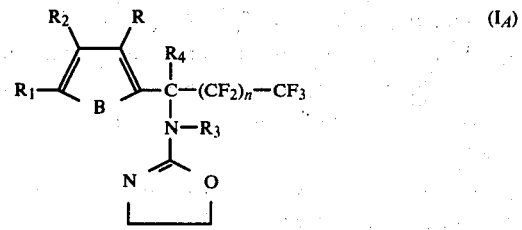

wherein the substituents $R_1$, $R_2$, $R_3$, $R_4$R and n are defined as above, and specifically
dl α-trifluoromethyl 2-[(furyl-2) methylamino]oxazoline
dl α-trifluoromethyl 2-(4-chlorobenzylamino)oxazoline
dl α-pentafluoroethyl 2-benzylamino oxazoline
dl α-trifluoromethyl 2-(4-methoxy benzylamino)oxazoline
dl α-trifluoromethyl 2-benzylamino oxazoline
-trifluoromethyl 2-benzylamino oxazoline(dextrorotatory isomer)
dl α-trifluoromethyl 2-(3-trifluoromethyl benzylamino)oxazoline
α-trifluoromethyl 2-benzylamino oxazoline (levorotatory isomer)
dl α-trifluoromethyl 2-[(thienyl-2)methylamino]oxazoline dl α-trifluoromethyl 2-(N-methylpyrrolyl-2)methylamino oxazoline.

dl α-trifluoromethyl 2-(2-methylbenzylamino)oxazoline.

dl α-trifluoromethyl 2-[(pyrrolyl-2) methyl amino] oxazoline dl α-trifluoromethyl 2-(N-methylbenzylamino) oxazoline.

(b) The thiazolines of formula $I_B$ in a racemic or optically-active form

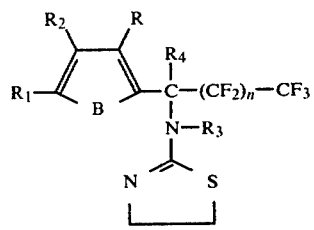

(I$_B$)

wherein the meanings of the substituents R, R$_1$, R$_2$, R$_3$, R$_4$, and n remain unaltered and specifically dl α-trifluoromethyl 2-benzylamino thiazoline (c) the tetrahydro m-oxazines of the formula $I_C$

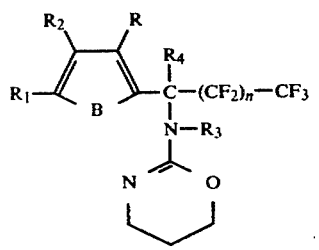

(I$_C$)

in which the definitions of the substituents R, R$_1$, R$_2$, R$_3$, R$_4$, and n remain the same as above in a racemic or optically-active form and specifically dl α-trifluoromethyl 2-benzylamino 4,5,6-tetrahydro 1,3-oxazine.

(d) The imidazolines of the formula $I_D$, in a racemic or optically-active form

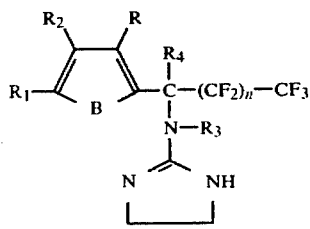

(I$_D$)

wherein the substituents R, R$_1$, R$_2$, R$_3$, R$_4$, and n are defined as above-given and specifically dl α-trifluoromethyl 2-benzylamino imidazoline.

(e) The tetrahydropyrimidines of formula $I_E$ in a racemic or optically-active form,

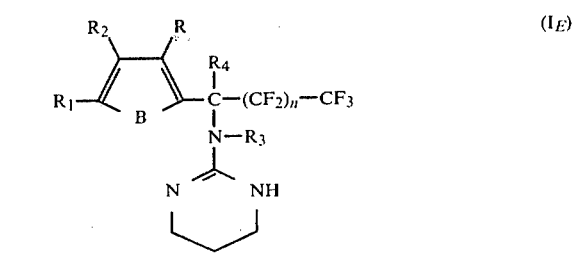

(I$_E$)

wherein the substituents R, R$_1$, R$_2$, R$_3$, R$_4$, and n are defined as above-given and specifically dl α-trifluoromethyl 2-benzylamino 4,5,6-tetrahydropyrimidine.

As far as this invention is concerned, the term lower alkyl denotes a hydrocarbon straight or branched chain having from 1 to 6 carbon atoms, optionally bearing a hydroxy, lower acyloxy, a lower alkoxy or a diethylamino substituent. Examples of lower alkyl radicals are methyl, butyl, isopentyl, n-hexyl or hydroxybutyl.

The term lower alkoxy denotes a lower alkyloxy radical wherein the term lower alkyl is similarly defined. Examples of such alkoxy radicals are methoxy, ethoxy, iso propoxy, sec butyloxy, néo pentyloxy, tert-butyloxy, n-hexyloxy, β-ethoxy β-ethoxy, diethylaminoethoxy radicals.

The term "halogen" designates a fluorine or a chlorine atom. It may be also a iodine or a bromine atom.

The compounds of formula I may be easily salified by adding a mineral or organic acid. Examples of suitable acids are hydrochloric acid, hydrobromic acid, sulphuric acid, phosphoric acid, nitric acid, formic acid, acetic acid, di-propyl acetic acid, tartaric acid, citric acid, maleic acid, pamoic acid, itaconic acid, benzoic acid, thiazole 5-carboxylic acid, nipecotic acid, glucose-1-phosphoric acid, methane sulphonic acid, isethionic acid and benzene sulphonic acid.

The compounds of formula I and the acid addition salts thereof are endowed with interesting pharmacological properties, namely hypotensive properties. They exert only very weak neutrological effects and may therefrom be used as a drug, namely as an anti-hypertensive drug without a fear of noxious side-effects, such as sedation or sleepiness.

This invention further extends to pharmaceutical compositions containing as active ingredient at least one compound of formula I or an acid addition salt thereof in admixture or conjunction with an inert non-toxic pharmaceutically-acceptable carrier or diluent.

The so-defined pharmaceutical compositions may be those intended for oral, parenteral, sublingual, percutaneous or rectal ways of administration. They are in the form of tablets, coated tablets, capsules, soft gelatine capsules, dragees, drinkable solutions or suspensions, drops; injectible suspensions or solutions, solutions in a polar solvent for percutaneaous use, sublingual tablets, suppositories and the like.

The injectible solutions or suspensions may be packed in the form of ampuls, multidosage flasks, or self-injectible syringes.

The useful posology may vary broadly depending on the age and the weight of the patient, the way of administration and the severity of the therapeutic indication. Usually in human medicine the posology may range from 0.1 mg to 2 mg per unit dosage and from 0.1 to 5 mg per day in the man. In veterinary medicine the pharmaceutical compositions may also be used and the amount of active ingredient is then adapted to the species to be treated.

The pharmaceutical compositions are prepared according to known methods. Among the inert carriers or diluents they may be particularly cited talc, the starches, magnesium stearate, calcium carbonate, magnesium phosphate, silica, lactose for the tablets, distilled water or saline solutions for the injectible solutions or suspensions, benzyl alcohol for the percutaneous solutions; cocoa butter or polyethylene glycol stearates for the suppositories.

This invention still provides a process for preparing the aryl (trifluoroethyl) amines of formula I

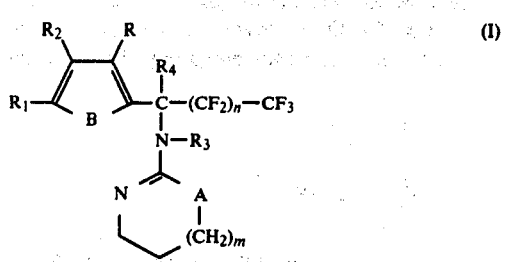

wherein the substituents R, $R_1$, $R_2$, $R_3$, $R_4$, A, B, n and m have the previously-given definitions and the acid-addition salts thereof in which an αaryl (trifluoroethyl) amine of formula II

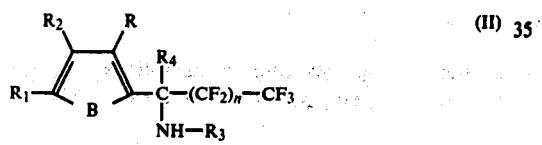

wherein the substituents B, R, $R_1$, $R_2$, $R_3$, $R_4$ and n have the previously-given meanings is condensed, *either* with a (ω-halogenoalkyl) isocyanate or isothiocyanate having the formula III.

$$A=C=N-(CH_2)_{m'}-CH_2Hal \qquad (III)$$

in which
A is oxygen or sulphur
Hal is a chlorine, bromine or iodine and
m' is an integer of 1 to 3
to produce a ω-halogeno alkyl Urea or thio-Urea of formula IV

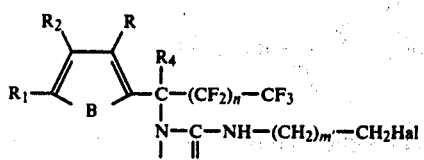

in which the substituents R, $R_1$ $R_2$, $R_3$, $R_4$, A, B, Hal, n and m' have the above-given definitions.

Which is cyclized by heating in an aqueous medium to form a compound of formula I'

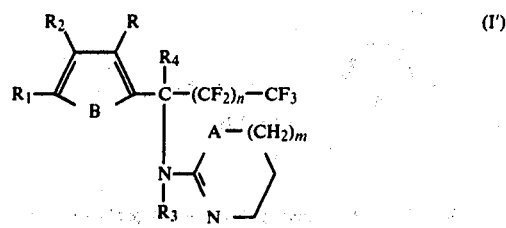

in which A is oxygen or sulphur and the substituents B, R, $R_1$, $R_2$, $R_3$, $R_4$, n and m have the above-given definitions, which may be further salified by adding a mineral or organic acid or resolved into their optical isomers by means of an optically-active organic acid.

*Either* with a S-methyl isothiourea of the formula V

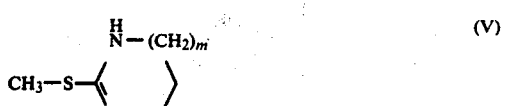

wherein m is defined as above-given, to produce a compound of formula I''

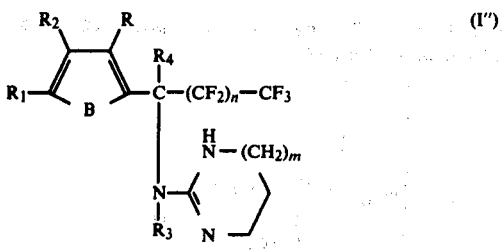

in which the substituents R, $R_1$, $R_2$, $R_3$, $R_4$, B, n and m are defined as previously given and for which A is an imino radical.

Which may be further salified by adding a mineral or organic acid or resolved into their optical isomers. Compounds of this invention according to formula I are also advantageously prepared by reacting an α-aryl(trifluoroethyl)amine of formula II with an(alkali-metal) thiocyanate in the presence of an acylating agent to produce an acylthioUrea of the formula VI

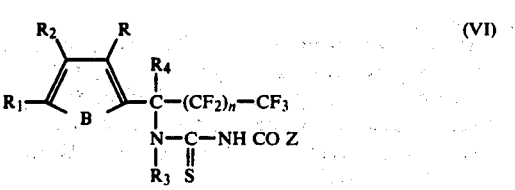

in which the substituents B, R, $R_1$, $R_2$, $R_3$, $R_4$ and n are defined as previously-given and Z is a lower alkyl radical, a phenyl radical or a phenyl radical substituted with a halogen or a lower alkoxy then saponifies the acyl radical in alkaline medium to produce a thiourea of the formula VII

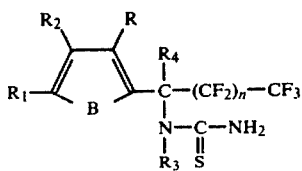

(VII)

in which the definitions of the substituents remain unaltered.

Which is further alkylated by means of an alkylating agent to form a S-lower alkyl thiourea of the formula VIII

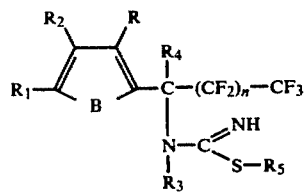

(VIII)

in which $R_5$ is a lower alkyl radical and R, $R_1$, $R_2$, $R_3$, $R_4$, B and n have the above-given definitions, condenses the latter with an alkylene diamine of the formual IX.

$$2HN-(CH_2)_p-NH_2 \quad (IX)$$

in which p is an integer of 2 to 4 and recovers a compound of formula (I''')

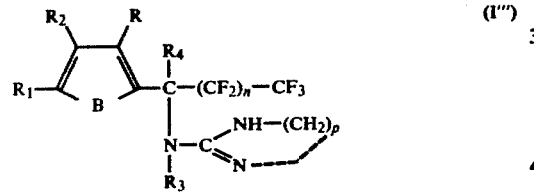

(I''')

wherein the definitions of the substituents remain unaltered.

Which may be further salified by adding a mineral or organic acid or resolved into their optical isomers.

The process according to the invention may also be defined by the following features, which are presently preferred:

(a) the condensation of an amine of formula II with an ω-halogenoalkyl isocyanate or isothiocyanate of formula III is performed in an inert organic solvent such as a linear or cyclic ether at a temperature of about 0° to about 10° C., (b) the cyclisation of the ω-halogenoalkyl Urea or thiourea of formula IV is performed by heating at a temperature ranging from 50° to 150°, preferably in an aqueous medium, in the presence or absence of a hydracid acceptor such as an alkalimetal carbonate or a trilower alkylamine, (c) the condensation of the amine of formula II with a S-methyl isothiourea of formula V is performed in a polar solvent such as pyridine, dimethylformamide, dimethyl acetamide, hexamethylphosphorotriamide and at a temperature ranging from 80° to 120°, (d) the S-methyl isothiourea of formula V is preferably used as an acid addition salt, providing a compound of formula I'' as a salt, (e) the alkali-metal thiocyanate is preferably ammonium thiocyanate, (f) the acylating agent is an acid chloride and more precisely a lower alkyl carboxylic acid chloride, benzoyl chloride, or a substituted benzoic acid chloride, (g) the saponification of the acylthiourea of formula VI is carried out by means of an alkalimetal hydroxide such as potash or soda, (h) the alkylating agent is a lower alkylhalide, a lower alkyl sulphate or a lower alkyl arylsulphonate such as methyl iodide or ethyl sulphate, (i) the condensation of the alkyl isothiourea of formula VIII with the lower alkylene diamine of formula IX is carried out by heating the reactants in a high-boiling solvent such as pyridine, butanol, or isopropanol.

This invention further includes a process for preparing the α-aryl trifluoroethylamines of formula II which consists in reacting a halogeno arene of the formula X

(X)

wherein the definitions of the substituents R, $R_1$, $R_2$ and B are those previously given and Hal is a chlorine or a bromine with a metal selected from the group consisting of magnesium and cadmium, to produce the corresponding organometallic derivative, condensing the latter with a trifluoroacetic acid of the formula XI $$CF_3-(CF_2)_n-COOH \quad (XI)$$

wherein n has the above-given definitions recovering an aryl trifluoromethylketone of the formula XII (XII)

wherein R, $R_1$, $R_2$, B and n have the above-given definitions which may either be condensed with a hydroxylamine derivative of the formula XIII $$2HN-OR_6 \quad (XIII)$$

in which $R_6$ is a hydrogen or a lower alkyl radical/to provide the corresponding oxime of the formula XIV (XIV)

in which the definitions of the substituents remain unaltered and reducing the latter by means of sodium in a lower alkanol, an alkalimetal mixed hydride or of diborane to obtain the desired compound of formula II in which $R_3$ and $R_4$ are hydrogen, or be condensed with a metal alkyl to produce a tertiary carbinol of the formula XV

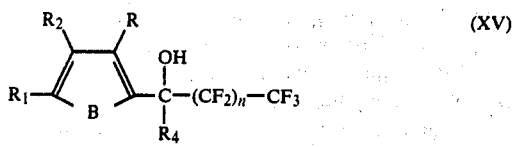

in which R, $R_1$, $R_2$, B and n have the above-given definitions, and $R_4$ is a methyl radical, an ethyl radical or a cyclopropyl radical reacting this compound with a cyanogen halide to form the corresponding carbamate, and hydrolysing the latter in acidic medium to produce a compound of formula XVI

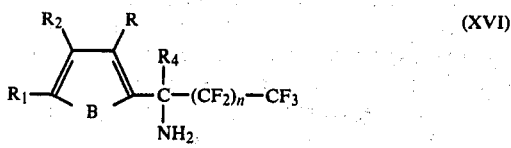

in which R, $R_1$, $R_2$, $R_4$ B and n have the above-given definitions and for which $R_3$ is a hydrogen.

In order to get an α-aryl(trifluoroethyl)amine of formula II in which $R_3$ is a methyl or ethyl radical, an α-aryl(trifluoroethyl)amine of formula II in which $R_3$ is hydrogen, is condensed with, formaldehyde or acetaldehyde then the resulting Schiff's Base is reduced into a N-methyl or ethyl derivative by means of catalytic hydrogenation or an alkali metal mixed hydride.

The N-methylation may also be performed by reacting the amino derivative with a lower alkyl chloroformate and reducing the resulting alkyl carbamate by means of an alkali metal mixed hydride to produce a N-methyl derivative.

In the process for producing the compounds of formula II the alkyl metal derivative is preferably an alkyl magnesium halide, an alkyl cadmium halide, an alkyl zinc halide, an alkyl mercury halide, or an alkyl copper halide.

The cyanogen halide is preferably a bromide or a chloride.

The hydrolysis of the isocyanate into the carbamate is carried out with a strong acid, preferably a mineral acid as for example hydrochloric acid or sulphuric acid.

The resolution of the compounds of formula I may be performed by salifying a compound of formula I in racemic form with an optically-active acid such as a carboxylic acid for example d-tartaric, NN dimethyl d-tartramic acid, d-camphoric acid, abietic acid, d-Ketogulonic acid, ascorbic acid, 1-menthoxyacetic acid; a sulphonic acid as for example d-camphosulphonic acid; a phosphoric acid as for example glucose 1-phosphoric acid, d-glucose 1,6-diphosphoric acid, an optically-active bis-naphtyl phosphoric acid.

The resolution may also be performed at an earlier step and namely on the ω-halogeno alkyl Ureas or thioureas of the formula IV or on aryl(trifluoroethyl)amines of the formula II. At these steps the same resoluting agents may be utilized as for the compounds of the formula I.

This invention further exends to the intermediate compounds used or produced during the performance of the processes:

(a) the oximes of formula XIV

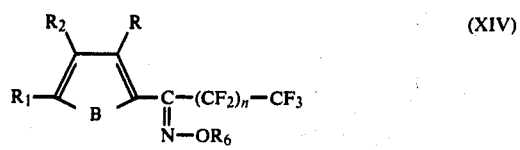

wherein the definitions of the substituents remain the same than those previously given (b) the aryl(trifluoroethyl)amines of formula II

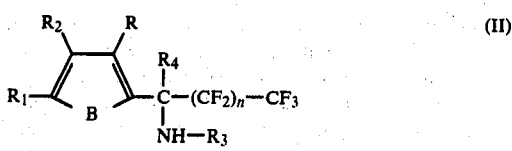

in which the definitions of the substituents R, $R_1$ $R_2$, B, $R_3$, $R_4$ and n remain unaltered, in a racemic or optically-active form, (c) the (ω-halogenoalkyl)Ureas or Thioureas of formula IV

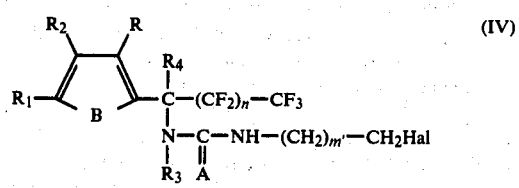

wherein the definitions of the substituents R, $R_1 R_2$, $R_3$, $R_4$, B, n, m' and Hal remain unaltered and A is oxygen or sulphur, (d) the n-acyl Thioureas of the formula VI

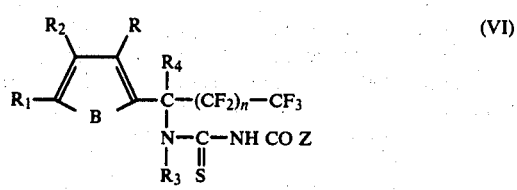

wherein the definitions of the substituents R, $R_1$, $R_2$, $R_3$, $R_4$, B and n remain unaltered and Z is a lower alkyl radical, a phenylradical or a phenyl radical substituted with a halogen or a lower alkoxy radical, (e) the thioureas of the formula VII

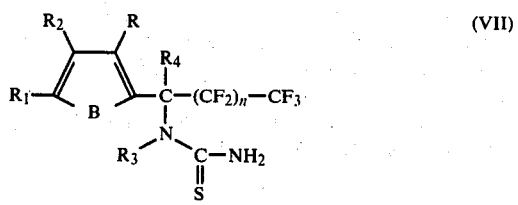

wherein the substituents R, $R_1$, $R_2$, $R_3$, $R_4$, B and n are defined as previously-given (f) the alkyl isothio Ureas of the formula VIII

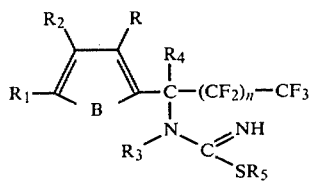

(VIII)

wherein R, R₁R₂, R₃, R₄, B and n are defined as above-given and R₅ is a lower alkyl radical.

It may also be of interest to produce the compounds of general formula XII in which B is an oxygen atom, a sulphur atom or an imino group N-R₅ by direct acylation of the corresponding aromatic derivative with an anhydride of the formula (CF₃(CF₂)ₙCO)₂O in a chlorinated solvent such as dichorethane or trichlorethane.

The following examples are merely intended to illustrate the invention. They do not limit it in any manner.

EXAMPLE I

α-phenyl 2-(trifluoroethylamino) imidazoline

Step A

N (α-phenyl trifluoroethyl) N'benzoylthio Urea 8.2 g ammonium thiocyanate are dissolved in 54 ml water and the resulting solution is cooled to about 0°. The temperature is kept to this temperature during the addition of a solution of 11.5 ml benzoyl chloride in 10.5 ml acetone thereto. The temperature of the reaction mixture is let to revert to about 30° then the mixture is heated to reflux for 10 mn. A solution of α-phenyl trifluoroethylamine in 110 ml acetone is thereafter added portionwise for 1 hour while heating the mixture at reflux. The heating is maintained for a further period of 1½ hour then let to revert to ambient temperature. The solvent is distilled off. The dry residue is taken up in 250 ml water. The aqueous solution is extracted 3 times with 200 ml ether. The organic phases are united, washed with water until the washings are free of chlorine ions, filtered and dried on sodium sulphate. The solvent is evaporated off, under reduced pressure and 34.1 g of raw product are recovered. The compound is purified by recrystallizing it from hexane. The pure N-(α-phenyl trifluoroethyl) N'-benzoyl thio Urea melts at 55°-60°.

Step B

In flask there are successively poured 31 g N-(α-phenyltrifluoroethyl) N'-benzoylthio Urea 175 ml ethanol and 27 ml N solution of sodium hydroxide. The whole mixture is kept under stirring for 36 hours at room temperature. Ethanol is thereafter evaporated under reduced pressure and it remains an oily residue which is twice extracted with 100 ml ether. The ethereous phases are united, whashed with water until neutral, dried, filtered then evaporated to dryness.

20.3 g of a raw product are thus recovered. Crystallisation is initiated by triturating with few ml of heptane.

14.9 g N-(α-phenyltrifluoroethyl) thio Urea are thus obtained i.e. a yield of 72%. The pure compound is further recrystallised from a mixture of cyclohexane-Benzene. It melts at 115°-125°.

Step C

N-(α-phenyltrifluoroethyl) S-methyl isothio Urea 14.5 g N-(α-phenyltrifluoroethyl) thio Urea are dissolved in 270 ml acetone and this solution is heated to reflux. A solution of 17.6 g methyl iodide in 7.75 ml acetone is added thereto while keeping the heating at reflux during the addition and for a further period of three hours. The solvent is thereafter evaporated off and 25 of an oily product is obtained. The crystallisation thereof is initiated by scratching in the presence of benzene. The crystalls melt at 138°-144°. A further crystallisation supplies 18.5 g of pure N-(α-phenyl trifluoroethyl) S-methylisothiourea in the form of its hydroiodide melting at 142°-144°.

The evaporation of the mother liquors provides a second crop weighing 3.8 g.

STEP D 2-(α-phenyltrifluoroethylamino) imidazoline, 0.88 g of ethylene diamine in 1 ml ethanol are added to a solution of 6.6 g N. (α-phenyl trifluoroethyl) S-methyl isothiourea (hydroiodide) in a mixture of ethanol and isoamyl alcohol. The mixture is heated to reflux until the precipitate disappears and the evolution of ammoniac and methyl mercaptan ceases. The reflux lasts about 6 hours and the solution is let to revert to room temperature, then kept in a cool place for a night. The solvent is thereafter evapored off. The crystallisation is initiated by scratching. The thus formed crystals are taken up in few ml isopropyl ether. By evaporating the solvent, 6.9 g of 2-(α-phenyltrifluoroethylamino) imidazoline (hydroiodide) are obtained. The product is purified by recrystallising from 15 ml ethyl acetate. The solution is filtered and evaporated off. A pure compound is obtained weighing 3.4 g and melting at 180°-190°. A further recrystallisation from water provides 3.1 g of 2. (α-phenyl trifluoroethylamino)imidazoline (hydroiodide) i.e. a yield of 49%. The analytical sample melts at 188°-190°.

The hydroiodide is further converted into the free base by adding a solution of sodium hydroxyde to it- 1.8 g of 2(α-phenyl trifluoroethylamino) imidazoline are obtained after recrystallisation from acetonirile in the cold. The compound melts at 178°-182° (sublim).

2-(α-phenyl trifluoroethylamino) imidazoline is soluble in the stoichiometric amount of N/10 hydrochloric acid solution.

| Analysis : C₁₁H₁₂F₃N₃ = 243.34 | | | |
|---|---|---|---|
| | C | H | N % |
| Calculated | 54.31 | 4.98 | 17.27 |
| Found | 54.54 | 5.37 | 17.21 |

EXAMPLE II dl 2-(α-trifluoromethyl benzylamino) tetrahydropyrimidine

Using the same procedure as in example I step D starting from 6.6 g of N-(α-phenyl trifluoroethyl) S-methyl isothiourea in 70 ml iso amyl alcohol and 1.3 g diaminopropane in 23 ml isoamyl alcohol, 3.9 g of [2-(α-phenyl (trifluoroethylamino)] tetrhydropyrimidine are obtained (i.e. a yield of 58%), as its hydroiodide. It melts at 196°-202° after recrystallisation from ethyl acetate then from water.

This hydroiodide is then converted into the free base by adding normal solution of sodium hydroxide. The free base is thereafter taken up in methylene chloride and added with an ethanolic solution of hydrochloric acid until the pH value reaches 2. The solvent is thereafter evaporated off and the oily residue is taken up with ethyl acetate from which it crystallises. The hydrochloride is further purified by recrystallising it from isopropanol. The pure hydrochloride melts at 206°–210°.

| Analysis : $C_{12}H_{14}F_3N_3$, ClH = 293.725 | | | | |
|---|---|---|---|---|
| | C | H | N | Cl % |
| Calculated | 49.07 | 5.16 | 14.29 | 12.07 |
| Found | 48.89 | 5.24 | 14.20 | 12.03 |

EXAMPLE III dl 2-[α-(trifluoromethyl) benzylamino] oxazoline

Step A dl N-(α-phenyl trifluoromethyl) N'-(αchloroethyl) Urea

A solution of 7.4 g of dl (α-phenyl trifluoroethyl)amine in 40 ml ether is added with a cool solution of 4.3 g β-chloroethyl isocyanate in 25 ml ether dropwise for 30 mn. During this addition the mixture is kept at 0° to −5° C. then kept under stirring for 24 hours at room temperature. The thus formed precipitate is filtered, washed with ether and dried-7.9 g of N-(α-phenyltrifluoroethyl) N'-(β-chloroethyl) Urea are isolated (i.e. a yield of 67%). The thus obtained compound melts at 127°–132°. It is used as such for the next step.

Step B 7.6 g of N-(α-phenyl trifluoroethyl) N'-(β-Chloroethyl) Urea are suspended in 60 ml water, then 4.3 ml triethylamine are added and the whole mixture is heated to reflux under stirring for 30 mn. The reaction mixture is let to revert to about 20°, the precipitate is separated which is dried, washed with water until the washings are neutral and dried under vacuum-6.3 g 2-[α-trifluoromethyl) benzylamino] oxazoline are obtained i.e. a yield of 95%. For analytical purpose the compound is recrystallized from isopropanol with a yield of 73%. The analytical sample melts at 162°–168° (sublim).

| Analysis $C_{11}H_{11}F_3N_2O$ = 244,22 | | | |
|---|---|---|---|
| | C | H | N % |
| Calculated | 54.10 | 4.54 | 11.47 |
| Found | 53.98 | 4.55 | 11.34 |

The starting compound, α-phenyl trifluoroethylamine is obtained according to the process described by R. A. Shepart J. org. Chem. 32 (1967) 3197.

EXAMPLE IV dl [(α-trifluoromethyl) (3-trifluoromethyl benzylamino)] oxazoline

Step A (3-trifluoromethyl phenyl) trifluoromethyl Ketoxine 7.8 g of hydroxylamine hydrochloride are dissolved in 250 ml of a mixture of ethanol and pyridine and to this solution 7 g (m-trifluoromethyl phenyl) trifluoromethyl Ketone are added. The mixture is heated to reflux for 16 hours, then cooled and diluted with 100 ml water. The oxime precipitates and is separated by filtration, dried, washed with water many times, and dried again. The yield amounts to 42%.

(3-trifluoromethyl phenyl) trifluoromethyl Ketoxime melts at 63°–65°.

The starting material (m-trifluoromethylphenyl) trifluoromethyl Ketone is obtained according to the process described by R-Fuks and G. J. Pork J. org. Chem. 22 (1957) 993

Step B dlα-(3-trifluoromethyl phenyl) (trifluoroethyl) amine 2.5 g (3-trifluoromethyl phenyl) trifluoromethyl Ketoxime are suspended in 40 ml isopropyl ether and to this suspension 4 g lithium aluminium hydride are added. The mixture is heated to reflux for 3 hours then cooled. The excess of reagent is destroyed by cautious addition of an aqueous solution of tartaric acid. The mixture is made basic by adding sodium hydroxide and the ethereous phase is separated. The aqueous phase is further extracted with isopropyl ether; the organic solutions are united, washed with water, dried an evaporated off under reduced pressure.

The residue is purified by fractional distillation -dlα-(3-trifluoromethyl phenyl) (trifluoroethyl) amine is thus obtained with a yield of 72%. This compound is a liquid which boils at 82°–83° under 15 mm Hg.

$n_D^{23}$ = 1,4250.

Step C dl N-[α-(3-trifluoromethyl phenyl) trifluoroethyl]N'-(βchloroethyl) Urea Using the same procedure as at step A of example III and starting from dl α-(3-trifluoromethyl) phenyl) trifluoroethyl) amine and β-chloroethyl isocyanate, N-[α-(3trifluoromethylphenyl) trifluoroethyl] N'-(β-chloroethyl) Urea is obtained with a theorectical yield. It melts at 124°–128°.

Step D dl 2-[α-(trifluoromethyl) (3-trifluoromethyl benzylamino)] oxazoline

Using the same procedure as in example III step B and starting from N-[α-(3-trifluoromethyl phenyl) trifluoroethyl] N'-(β-chloroethyl) Urea, dl 2-[α-(trifluoromethyl) 3-trifluoromethyl benzylamino)] oxazoline is produced. It melts at 129°–132°.

| Analysis $C_{12}H_{10}F_6N_2O$ = 312,22 | | | |
|---|---|---|---|
| | C | H | N % |
| Calculated | 46.16 | 3.23 | 8.96 |
| Found | 46.45 | 3.48 | 8.85 |

EXAMPLE V dl 2-(α-trifluoromethyl benzylamino) 4,5,6-tetrahydro 1,3/oxazine

Step A dl N-[α-phenyl(trifluoroethyl)] N'-(δ-chloropropyl) Urea

Using the same procedure as in example III at step A and starting from dl α-phenyl (trifluoroethyl) amine and δ-chloropropyl isocyanate dl N-[α-phenyl (trifluoroethyl)] N'-(δ-chloropropyl) Urea is obtained with a quantitative yield and is used as such for the next step.

Step B dl 2-(α-trifluoromethyl benzylamino) 4,5,6-tetrahydro 1,3-oxazine

Using the same procedure as in example III at step B, dl 2-(α-trifluoromethyl benzylamine) 4,5,6-tetrahydro 1,3-oxazine is obtained with a yield of 30%. This compound melts at 113°–115° (isopropyl ether)

| Analysis $C_{12}H_{13}F_3N_2O$ = 258,24 | | | |
|---|---|---|---|
| | C | H | N % |
| Calculated | 55,81 | 5,01 | 10,85 |
| Found | 55,32 | 5,29 | 10,65 |

EXAMPLE VI dl 2-(αtrifluoromethyl benzylamino) thiazoline 7.1 g of dl α-phenyl (trifluoroethyl) amine are dissolved in 75 ml dimethyl formamide and 26 g of 2-methylthiothiazoline are added thereto. The mixture is heated to reflux for 1 hour then let to revert at ambient temperature. The mixture is diluted with an equal volume of isopropyl ether. Crystallisation of the hydroiodide is initiated by scratching then the crystalline suspension is kept in the refrigerator for a night.

The crystals are succione-filtered, dried, washed with a little isopropyl ether and dried under vacuum.

The dl B 2-(trifluoromethyl benzylamino) thiazoline hydroiodide is dissolved in water converted into its base by adding sodium carbonate until basic. The aqueous mixture is extracted three times with isopropyl ether. The organic phases are united, washed with water, dried, filtered and distilled off.

dl 2-(α-trifluoromethyl benzylamino) thiazoline is thus obtained. After recrystallisation from acetonitrile it melts at 165°–168°.

| Analysis $C_{11}H_{11}F_3N_2S$ = 260,28 | | | | |
|---|---|---|---|---|
| | C | H | N | S % |
| Calculated | 50.75 | 4.26 | 10.77 | 12.32 |
| Found | 50.60 | 4.37 | 10.83 | 12.75 |

EXAMPLE VII dl 2-α-trifluoromethyl (4-methoxy benzylamino) oxazoline

Melting point at 149°–155° (isopropanol).

EXAMPLE VIII dl 2-[α-pentafluoroethyl benzylamino] oxazoline

Using the procedure of example IV and starting from pentafluoro propiophenone the following compounds have been obtained.

(a) pentafluoropropiophenone Ketoxime MP 53° then 70° (yield 75%)

(b) dl α-phenyl(pentafluoropropyl) amine
BP = 82°–90°/18 mmHg.
yield = 70%.
Its hydrochloric acid addition salt melts at 178°–186°.

(c) dl N-[αphenyl (pentafluoropropyl)] N'-(β-chloroethyl) Urea
MP = 78°–82°.
yield = 70%.

(d) dl 2-[α-pentafluoroethyl benzylamio] oxazoline
MP = 181°–183° (isopropanol).

| Analysis $C_{12}H_{11}F_5N_2O$ = 294.30 | | | |
|---|---|---|---|
| | C | H | N % |
| Calculated | 48.99 | 3.77 | 9.52 |
| Found | 49.09 | 4.01 | 9.49 |

The starting material pentafluoropropiophenone is obtained according to the process described by K. T. Duhart J of Am Chem Soc 78 (1956) 2268.

EXAMPLE IX

Using the procedure of example IV the following compounds have been obtained (a) (4-chlorophenyl) trifluoromethyl Ketoxime
F = 68°–72°.
yield = 85%.

(b) dl [α-(4-chlorophenyl) trifluoroethyl] amine
BP = 104°–107°/12 mm Hg.
MP = 29°–34°.
Its hydrochloride melts at 182°–189°.

(c) dl N-[α-(4-chlorophenyl) trifluoroethyl] N'-(β-chloroethyl) Urea
MP = 142°–145°.
yield = 75%.

(d) dl 2-[α-trifluoromethyl (4-chlorobenzyl) amino] oxazoline
MP = 158°–163°.

| Analysis $C_{11}H_{10}ClF_3N_2O$ = 278,66 | | | | |
|---|---|---|---|---|
| | C | H | N | Cl % |
| Calculated | 47.41 | 3.62 | 10.05 | 12.72 |
| Found | 47.26 | 3.61 | 9.87 | 12.61 |

EXAMPLE X dl 2-[α-trifluoromethyl (furyl-2) methylamino] oxazoline

Using the same procedure as in example IV and starting from (furyl-2) trifluoromethyl Ketone obtained according to S. Clementi Ric. Sei. 37 (1967) 418, the following compounds have been obtained.

(a) (furyl-2) trifluoromethyl Ketoxime
MP = 103°–106°

(b) dl α-(furyl-2) trifluoroethyl amine
BP = 64°–68°/20 mm Hg.
$n_D^{20}$ = 1,4175.
Its hydrochloride melts at 139°–145°.

(c) dl N-[α-furyl-2) trifluoroethyl] N'-(β-chloroethyl) Urea
MP = 107°–113°.
yield 80%.

(d) dl 2-[αtrifluoromethyl (furyl-2) methylamino] oxazoline.
MP = 112°–119° (sublim.) from isopropyl ether.

| $C_9H_9F_3N_2O_4$ = 234,17 | | | |
|---|---|---|---|
| | C | H | N % |
| Calculated | 46,15 | 3,87 | 11,96 |
| Found | 46,10 | 3,94 | 11,81 |

This compound is soluble in the stoechiometric amount of dilute hydrochloric acid giving rise to the hydrochloride.

EXAMPLE XI dl 2-[αtrifluoromethyl (thienyl-2) methylamino] oxazoline

Step A (thienyl-2) trifluoromethyl O-methyl Ketoxime

Using the same procedure as in step A of example IV and starting from α-thienyl trifluoromethyl Ketone (described by S-Clementi Ric. Sci. 37 (1967) 418).

(thienyl-2) trifluoromethyl O-methyl Ketoxime is obtained as a liquid boiling at 78°–82°/20 mm Hg.
$n_D^{24} = 1,4920$.

Step B dl α-(thienyl-2) trifluoroethyl amine/the O-methyl Ketoxine of step A is reduced by means of diborane in ether, giving rise to the corresponding amine with a yield of 85%.

dl α-(thienyl-2) trifluoroethylamine is a liquid boiling at 79°–81°/20 mm Hg.
$n_D^{20} = 1,6320$.

Its hydrochloride melts at 160°–162° (sublim.)

Step C dl N-[α-(thienyl-2) trifluoroethyl] N'-(β-chloroethyl) Urea

Using the same procedure as in example III step A the β-chloroethyl Urea is obtained with a yield of 70%. This compound is used as such for the next step of the synthesis.

Step D dl 2-[α-trifluoromethyl (thienyl-2)methylamino]oxazoline

Using the same procedure as in example III step B the oxazoline is obtained with a yield of 65%.

dl 2-[α-trifluoromethyl (thienyl-2) methylamino]oxazoline after recrystallisation from ether melts at 138°–145°.

| Analysis $C_9H_9F_3N_2OS$ = 250.24 | | | | |
|---|---|---|---|---|
| | C | H | N | S % |
| Calculated | 43.20 | 3.63 | 11.20 | 12.82 |
| Found | 43.12 | 3.77 | 11.17 | 13.02 |

EXAMPLE XII levorotatory 2-[α-trifluoromethyl benzyl amino] oxazoline

Step A

A vorotatory α-phenyl trifluoroethylamine 45 g d-tartaric acid are dissolved in 185 ml water. To this solution 52.5 g of dl α-phenyl trifluoroethyl amine are added portionwise for 6 hours while keeping a strong stirring. The mixture is thereafter kept aside for 12 hours. The precipitate of d-tartarate is succionfiltered and dried in an oven in the vaccum. 51 g of d-tartarate are thus recovered melting at 115° then 132°. Two further recrystallisations from water increase the melting points to 118° and 134°. The optical purity of the d-tartarate is determined by TLC using the Mosher's Reagent as revealing agent. The purity is at least 96.5%.

The rotatory power of the d-tartarate is:
$[\alpha]_{578}^{24} = -7°1$ (C=5% MeOH).
$[\alpha]_{365}^{24} = -41°5$ (C=5% MeOH).

The d-tartarate is converted into the free base by adding enough sodium hydroxide and extracting the resulting precipitate by ether. After evaporation of the solvent, 10.7 g of laevorotatory α-phenyl trifluoroethylamine are recovered.
BP=72–74/14 mm Hg.
yield=86%.
$[\alpha]_{578}^{25} = <22.1°$ (C=1% MeOH).
$[\alpha]_{365}^{25} = "65.5°$ (C=1% MeOH).

The laevorotatory isomer crystallises at a temperature lower than 30°.

Step B

Laevorotatory N-[α-phenyl (trifluoroethyl)] N'-(βchloroethyl) Urea

Using the same procedure as in example III step A N-[αphenyl (trifluoroethyl)] N'-(β-chloroethyl) Urea (laevorotatory isomer) is obtained with a quantitative yield. It melts at 149°–151°.
$[\alpha]_{589}^{23} = -38.1°$ (methanol).
$[\alpha]_{265}^{23} = -141°$ (methanol).

Step C laevoratory 2-[αtrifluoromethyl) benzylamino] oxazoline

Using the same procedure as in example III step B 2-[α-(trifluoromethyl) benzylamino] oxazoline (laevorotatory isomer) is obtained. It melts at 125°–133° (sublim.) after recrystallisation from isopropanol.
$[\alpha]_{589}^{22} = -87.4°$ (C=1% ethanol).
$[\alpha]_{365}^{22} = -335°$ (C=1% ethanol).

| Analysis $C_{11}H_{11}F_3N_2O$ = 244,22 | | | |
|---|---|---|---|
| | C | H | N % |
| Calculated | 54.10 | 4.54 | 11.47 |
| Found | 54.36 | 4.87 | 11.39 |

Laevorotatory 2-[α(trifluoromethyl) benzylamino] oxazoline is soluble in dilute hydrochloric acid. By evaporing the solvent off, the hydrochloride is recovered.

EXAMPLE XIII dextrorotatory 2-[(α-trifluoromethyl) benzylamino] oxazoline

From the mother liquors of the d-tartarate, the d-tartarate of the dextrorotatory isomer is recovered by concentration. It is further converted into the free base.
BP=74°–75°/15 mm Hg.
$[\alpha]_{589}^{25} = +23.5°$ (C=1% methanol).
$[\alpha]_{365}^{23} = +69.8°$ (C=1% methanol).

dextroratatory α-phenyl trifluoroethylamine is then converted into N-[αphenyl(trifluoroethyl)] N'-(βchloroethyl) Urea (dextrorotatory isomer) which melts at 148°–151° (yield 83.5%).
$[\alpha]_{589}^{23} = +38.2°$ (methanol).
$[\alpha]_{365}^{23} = +141.7°$ (methanol).

The β-chloroethyl urea is cyclised into the oxazoline by heating in the presence of aqueous triethylamine. Dextrorotatory 2-[(α-trifluoromethyl) benzylamino] oxazoline melts at 127°–132° (from isopropanol)
$[\alpha]_{589}^{22} = +87°6$ (C=1% ethanol).
$[\alpha]_{365}^{22} = +335.8°$ (C=1% ethanol).

| Analysis C₁₁H₁₁F₃N₂O = 244,22 | | | |
|---|---|---|---|
| | C | H | N % |
| Calculated | 54.10 | 4.54 | 11.47 |
| Found | 53.94 | 4.84 | 11.45 |

EXAMPLE XIV dl α-trifluoromethyl 2-[(N-methylpyrrolyl-2) methyl amino] oxazoline

Step A (N-methyl pyrrolyl-2) trifluoromethyl Ketone

In a boiler under pressure 81 g N-methyl pyrrole 241 g trifluoro acetic anhydride and 350 ml dichloroethane are introduced. The mixture is kept at about 100° for 12 hours therein. The inner temperature is let to revert to ambient temperature and the solvent is evaporated off. The dark residue is taken up in ether, the insoluble matters are segerated by filtration and the clear filtrate is evaporated off. The oily residue weighing 198 g is purified by fractional distillation under reduced pression — 12 g of a fraction boiling at 69°–71°/15 mm Hg is recovered. The yield amounts of 72%.

(N-methylpyrrolyl-2) trifluoromethyl Ketone is a liquid.

$n_D^{24} = 1,4572$.

Infra Red Spectrum: compatible with the proposed structure.

Stretchings at 1670 cm⁻¹ (carbonyl band).
Stretchings attributed to the CF₃ group.
NMR spectrum: in accordance with the proposed structure.

2 protons of the ring at 7.3 ppm.
1 proton of the ring at 6.4 ppm.
3 protons of the methyl group singulet at 4,0 ppm.

This compound gives rise to only one peak in VPC.

Step B (N-methyl pyrropyl-2) trifluoromethyl Ketoxime

Using the same procedure as in example IV step A and starting from (N-methyl pyrrolyl-2) trifluoromethyl Ketone, the corresponding Ketoxime is obtained with a yield of 45%.

MP = 69°–71° (sublim).

| Analysis C₇H₇F₃N₂O = 192.15 | | | |
|---|---|---|---|
| | C | H | N % |
| Calculated | 43.76 | 3.76 | 14.58 |
| Found | 43.72 | 3.76 | 14.36 |

Step C dl [(N-methylpyrrolyl-2) methyl]α-trifluoromethyl amine

Using the same procedure as in example IV step B and starting from 11 g of the Ketoxime of step B, dl [(N-methylpyrrolyl-2) methyl] α-trifluoromethyl amine is obtained. It boils at 84°–90°/18 mm Hg. Its hydrochloride melts at 150° then 168° (dec).

| Analysis C₇H₉N₂F₃ClH = 214,65 | | | | |
|---|---|---|---|---|
| | C | H | N | Cl % |
| Calculated | 39.34 | 4.72 | 13.11 | 16.60 |
| Found | 39.33 | 4.82 | 13.01 | 16.45 |

Step D dl N-[2-N(methylpyrrolyl-2) trifluoroethyl] N'-(β-chloroethyl) Urea

Using the same procedure as in example III step A and starting from 3.45 g of dl [(N-methyl pyrrolyl-2) methyl] α-trifluoro methyl amine, hydrochloride, 2.7 g of the β-chloroethyl Urea are obtained in two crops, melting at 131°–136°.

Infra Red spectrum: in accordance with the structure.
Stretchings at 3300 and 3360 cm⁻¹ (band NH).
Stretchings at 1640 and 1570 cm⁻¹ (band carbonyl).

Step E dl-α trifluoromethyl 2-[(N-methylpyrrolyl-2) methylamino] oxazoline

Using the same procedure as in example III step B, the oxazoline is obtained with a yield of 37%. It melts at 156°–167° (sublim).

This compound is soluble in a N/10 aqueous solution of hydrochloric acid.

| Analysis C₁₀H₁₂F₃ON₃ = 244,01 | | | |
|---|---|---|---|
| | C | H | N % |
| Calculated | 48.58 | 4.89 | 16.99 |
| Found | 48.51 | 4.94 | 16.78 |

Infra Red spectrum: in accordance with the proposed structure.

Stretchings at 3300 and 2500 cm⁻¹ (—NH).
Stretchings at 1700 cm⁻¹ (—C=N).

EXAMPLE XV dl α-trifluoromethyl 2-(N-methylbenzylamino) oxazoline

Step A dl N-methoxycarbonyl α-trifluoromethyl benzylamine

In three-neck flask they are successively introduced 35 g α-phenyl trifluoroethylamine, 20.2 g triethyl amine, 200 ml tetrahydrofuran then a solution of 19 g methyl chloroformate in 40 ml tetrahydrofuran while cooling at about 5°–10°. The temperature of the mixture is kept at about 5° for 1 hour then let to revert to about 20°. The appeared precipitate is separated by filtration and the filtrate is evaporated by dryness —45.3 g of a raw product are obtained which are purified by recrystallisation from isopropanol.

dl N-methoxycarbonyl α-trifluoromethyl benzylamine melts at 90°–94°.

Infra spectrum: in accordance with the structure.
stretchings at 3300 cm⁻¹.
stretchings at 1680 cm⁻¹ (carbonyl band).

Step B dl N-methyl α-trifluoromethyl benzylamine. In a flask 9.5 g lithium aluminium hydride and 100 ml tetrahydrofuran are added, then slowly a solution of 23.3 g of dl N-methoxycarbonyl α-trifluoromethyl benzylamine in 100 ml tetrahydrofuran is poured thereto. The whole mixture is heated to reflux for 6 hours. After cooling, the excess of reagent is destroyed by cautious addition of a dilute solution of sodium hydroxide, then of water. The appeared precipitate is separated by filtration, washed with few ml of tetrahydrofuran and the washings are added to the filtrate. The organic solutions are evaporated to dryness and the dry residue weighing about 14 g is taken up in methylene chloride. After renewed extractions with 20% hydrochloric acid and basification of the acid solutions by addition of sodium hydroxide, an oily residue is recovered. It is further dissolved in ether, the ethereous solution is washed with water, dried on sodium sulphate, filtered and evaporated off — 8.4 g dl N-methyl α-trifluoromethyl benzylamine are recovered in the form of a colourless liquid boiling at 68°–70°/12 mm Hg $n_D^{22} = 1,4560$.

| Analysis $C_9H_{10}NF_3 = 189,2$ | | | |
|---|---|---|---|
| | C | H | N % |
| Calculated | 57.13 | 5.33 | 7.40 |
| Found | 57.02 | 5.37 | 7.02 |

Infra-Red spectrum: lack of carbonyl band.

Step C dl N-[N-methyl(α-phenyl)trifluoroethyl]N'-(β-chloroethyl Urea

Using the same procedure as in example IV step A, 9.2 g of the corresponding β-chloroethyl Urea are obtained, melting at 70°–80°.

| Analysis $C_{12}H_{14}N_2ClF_3 = 275,47$ | | | | |
|---|---|---|---|---|
| | C | H | N | Cl % |
| Calculated | 48.90 | 4.79 | 9.51 | 12.04 |
| Found | 48.36 | 4.92 | 9.65 | 11.98 |

Step D dl N-methyl 2-(α-trifluoromethylbenzylamino)oxazoline 8.4 g of dl N-[N-methyl(α-phenyl)trifluoroethyl]N'-(β-chloroethyl)Urea are suspended in 77 ml water 7 ml triethylamine are added thereto and the mixture is heated to reflux for 2½ hours. After cooling in an ice-bath, an oily product precipitates. It is extracted four times with methylene chloride. The methylenic solutions are united and extracted with hydrochloric acid. The aqueous phase is separated, then made basic by adding enough ammonia. The so-formed suspension is let in a cool place for a night. The insoluble matters are separated and taken up in methylenechloride. The methylenic phase is purified as usual and evaporated off — 6.1 g of an oily product are recovered which is purified by dissolving it in the minimal amount of ether and filtering the organic solution.

After evaporation of the solvent 4.7 g of pure dl N-methyl 2-(α-trifluoromethyl benzylamino)oxazoline are obtained as a viscous liquid soluble in the most of the organic solvents and in an aqueous solution of hydrochloric acid.

Infra Red spectrum: in accordance with the structure. stretchings at 1650 cm$^{-1}$ (group C=N).

lack of Carbonyl band.

EXAMPLE XVI dl α-trifluoromethyl 2-[(pyrrolyl-2)methylamino]oxazoline

Using the same procedure as in example XIV and starting from (pyrrolyl-2) trifluoromethyl Ketone, they are obtained:

O-methyl(pyrrolyl-2)trifluoromethyl Ketoxime
dl α-trifluoromethyl(pyrrolyl-2)methylamine
dl N-[α-trifluoromethyl(pyrrolyl-2)methyl]N'-(β-chloro ethyl)Urea.
dl α-trifluoromethyl 2-[(pyrrolyl-2)methyl amino]oxazoline.

MP = 125°–132° (from ether).

This compound is soluble in the stoichiometric amount of N/10 aqueous solutions of hydrochloric acid.

| Analysis $C_9H_{10}F_3N_3O = 233,19$ | | | |
|---|---|---|---|
| | C | H | N % |
| Calculated | 46.35 | 4.33 | 18.03 |
| Found | 46.33 | 4.46 | 17.82 |

NMR Spectrum: in accordance with the structure

| 5 | aromatic protons at 7.4 ppm |
|---|---|
| 1 | proton —CH quadruplet ar 5.9 ppm |
| 2 | methylenic protons CH$_2$—O at 4.3 ppm |
| 2 | methylenic protons CH$_2$—N = at 3.8 ppm |
| 3 | protons due to the methyl N singulet at 2.8 ppm CH$_3$ |

EXAMPLE XVII

Tablets containing 1 mg dl 2-[(α-trifluoromethyl benzylamino)]oxazoline

| | |
|---|---|
| dl 2-[(α-trifluoromethyl benzylamino)] oxazoline | 10 g |
| Mais starch | 250 g |
| Wheat starch | 50 g |
| Carboxymethyl starch | 20 g |
| Calcium carbonate | 120 g |
| Calcium phosphate | 140 g |
| Ethyl cellulose | 4 g |
| Talc | 4 g |
| Magnesium stearate | 2 g |

For 10.000 tablets weighing about 0.060 g each.

EXAMPLE XVIII

Pharmacological study of the compounds according to the invention (a) determination of the acute toxicity The average lethal dosage (LD$_{50}$) is determined on batches of mice (swiss strain) weighing about 20 g, by intraperitonal injections of increasing doses of the compounds to be tested.

The animals are kept under survey for 8 days and the deaths, if any, are numbered. The lethal dosage is graphically determined according to the method of Tainter and Miller.

The compounds of general formula I have been injected at doses ranging from 20 to 200 mg/Kg. In general the lethal dosage is about 200 mg/Kg. The only manifestations of toxicity in the animals are sedation and piloerection.

(b) determination of the hypotensive activity

The compounds of general formula I have been tested for hypotensive activity in lots of dogs, previously anesthetized with intravenous abutal which received the compound to be tested at doses ranging from 2 to 0.5 mg/Kg by intravenous way. At the lowest doses the decrease of the in arterial pressure is only short-lasting but the cardiac rhythm is significantly decreased for a period of about 30 mm.

Higher doses induce at first a slight increase of the arterial pressure then a significant decrease. The cardiac rhythm is largely depressed and this decrease may be as high as 50% of the normal cardiac rhythm observed in the controls.

(c) search of a neurological effect in the mice (strain CD) doses of 10 and 20 mg/Kg through intravritoneous way induce only a decrease of the motility, a decrease of a body temperature, a decrease in the food and drink intake.

In the rats (strain LE), small doses induce a state of excitation, and pilo-erection. Higher doses induce a decrease of the motility and of the muscular tone.

In the cats the administration of the compounds induce at first citation then a weak depressive state.

Therefore the compounds of general formula I appear to be imulant agent of the central noradrenergic receptors and they cause inhibition of the sympathic tone, hypotension and brady cardia. They are active parenterally as well as per oral way.

EXAMPLE XIX

Preparation of dl 2-[(2-methylphenyl)α-trifluoroethyl]amino zoline and its fumaric acid addition salt Step A 3-methyl trifluoroacetophenone In a three-neck flask fitted with mechanical stirring device and a pipe for an inert gas 41 g. of o, bromotoluene 300 ml ether are mixed together until a clear solution is obtained 5.85 g magnesium turnings then few crystalls of iodine are cautiously added. The mixture is heated to reflux under stirring. When all the magnesium has reacted the mixture is let to revert to room temperature and a solution of 6,16 ml trifluoroacetic acid in 15 ml ether is slowly added in about 10 mn. After completion of the addition the mixture is heated to reflux for 1.30 h and kept thereafter aside for 36 hours. The reaction mixture is poured on a mixture of 150 g crushed ice and 24 ml 30% hydrochloric acid. The ethereous phase is separated and the aqueous phase is extracted twice with 25 ml ether. The organic phases are united, washed with water, with an aqueous solution of sodium bicarbonate and further with water until the washings are neutral.

The solution is dried an sodium sulphate, filtered and distilled off. The dry residue is further purified by fractional distillation under reduced pressure. The fraction distilling at 60°–100° under 35 mm Hg is recovered. A renewed distillation allows the obtention of the main fraction boiling at 80°–85° under 35 mm Hg. This fraction weighs 9.1 g i.e. a yield of 60%.

INFRA-RED SPECTRUM:
Stretching at 1710 cm$^{-1}$ (carbonyl function).

Weak absorption at 3600–3800 cm$^{-1}$ in occordance with the structure.

Step B (2-methylphenyl)trifluoromethyl ketoxime

Using the same procedure as in example IV step A and starting from 7.5 g of 2-methyl trifluoroacetophenone, there was obtained 4.75 g of the corresponding oxime. It melts at 63.65°.

Step C dl[(2-methylphenyl)ααα-trifluoroethyl]amine

Using the same procedure as in example IV step B and starting from 4 g (2-methylphenyl)trifluoromethyl ketoxime, 2.8 g [(2-methylphenyl)ααα-trifluoroethyl]amine are obtained as an oil.

Step D dl N-[(ααα-trifluoromethyl) (2 methylphenyl)N'-(α-chloroethyl)]Urea

Using the procedure of example III Step A and starting from dl[(2-methylphenyl)ααα-trifluoroethyl]amine, dl N-[(2-methylphenyl)ααα-trifluoromethyl]N'-(β-chloroethyl)Urea is obtained with a yield of 78%. It is used as such for the next step of the synthesis.

Step E dl 2-[(2-methylphenyl)αααtrifluoroethyl]amino oxazoline

Using the same procedure as in example XV Step D and starting from the total amount of dl N-[(2 methylphenyl)ααα-trifluoromethyl]N'-(β chloroethyl)Urea obtained at Step D, 1.41 g of dl 2-[(2-methylphenyl)ααα-trifluoroethyl]amino oxazoline are produced as a liquid soluble in the usual organic solvents and in the aqueous solution of mineral acids.

Step F

Production of the fumaric acid salt 0.53 g of the oxazoline of step D is dissolved in 5 ml ether. To this solution a solution of 0.25 g fumaric acid in 4 ml ether is dropwise added. Crystallisation is initiated by scratching and the mixture is kept aside for a night in a cool place.

The crystalls are succion-filtered, washed with the minimal amount of ether and dried in vaccuo. Thus 0.42 g of the acid fumarate is obtained as white crystals which melts at 135°–137°. For analytical purposes the acid fumarate is recrystallized from acetonitrile. The melting point remains unaltered.

What we claim is:

1. The oxazoline(trifluoroethyl)amines of the formula

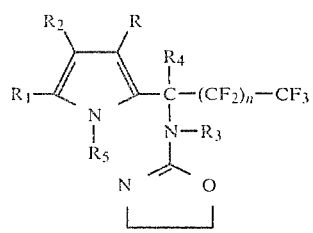

wherein

R₁ and R₂, the same or different, are hydrogen, a lower alkoxy radical of 1 to 6 carbon atoms, inclusive, a lower alkylradical of 1 to 6 carbon atoms, inclusive, or a halogen, R₃ is hydrogen, a methyl or an ethyl radical, R₄ is hydrogen, a methyl, an ethyl or a cyclopropyl radical, R is a hydrogen when R₁ and/or R₂ are different from hydrogen, or is a lower alkyl of 1 to 6 carbon atoms, inclusive, when R₁ and/or R₂ are hydrogen, R₅ is hydrogen or a lower alkyl radical of 1 to 6 carbon atoms, inclusive, and n is zero, 1 or 2.

2. The salts of a compound of formula I with mineral or organic acid, preferably a therapeutically-compatible mineral or organic.

3. The optically-active isomers of a compound of formula I or an acid addition salt thereof.

4. An of formula I₄, in racemic or form

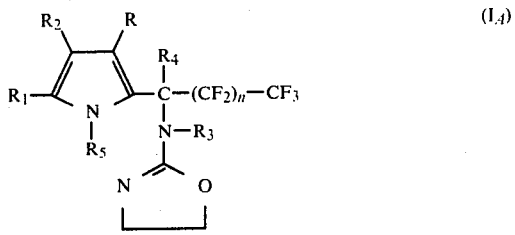

(I₄)

wherein the substituents R, R₁, R₂, R₃, R₄ and n are defined according to claim 1.

5. dlα-trifluoromethyl 2-(N-methylpyrrolyl-2)methylamino oxazoline according to claim 1.

6. dl α-trifluoromethyl 2-[(pyrrolyl-2)methyl amino]oxazoline according to claim 1.

* * * * *